United States Patent
Lee et al.

(10) Patent No.: US 8,991,238 B2
(45) Date of Patent: Mar. 31, 2015

(54) PORTABLE DIGITAL READER FOR URINALYSIS

(75) Inventors: Dae Sik Lee, Daejeon (KR); Hyun Woo Song, Daejeon (KR); Byoung Goo Jeon, Daejeon (KR); Min Joon Kim, Daejeon (KR); Moon Youn Jung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 25 days.

(21) Appl. No.: 13/390,596

(22) PCT Filed: Mar. 5, 2010

(86) PCT No.: PCT/KR2010/001386
§ 371 (c)(1),
(2), (4) Date: Feb. 15, 2012

(87) PCT Pub. No.: WO2011/030982
PCT Pub. Date: Mar. 17, 2011

(65) Prior Publication Data
US 2012/0152002 A1 Jun. 21, 2012

(30) Foreign Application Priority Data
Sep. 9, 2009 (KR) .................. 10-2009-0084930

(51) Int. Cl.
*G01N 21/00* (2006.01)
*G01N 33/493* (2006.01)
(Continued)

(52) U.S. Cl.
CPC .......... *G01N 33/493* (2013.01); *G01N 21/8483* (2013.01); *G01N 15/06* (2013.01); *G01N 2201/0221* (2013.01)
USPC .......... 73/61.48; 73/1.02; 422/50; 422/82.05; 422/561; 422/563; 422/82.11

(58) Field of Classification Search
CPC ............... A61B 5/0077; A61B 5/0095; A61B 5/04012; A61B 5/14532; A61B 5/1495; A61B 5/14865; A61B 5/6849; G01N 33/48771; C12Q 2525/301; C12Q 1/6813; C12Q 1/6827; B01L 3/502761
USPC ............... 73/61.48, 1.02; 422/50, 82.05, 561, 422/563, 82.11
See application file for complete search history.

(56) References Cited

U.S. PATENT DOCUMENTS

| 6,183,694 B1 | 2/2001 | Radtke et al. |
| 7,416,700 B2 * | 8/2008 | Buechler et al. ........... 422/82.08 |

(Continued)

FOREIGN PATENT DOCUMENTS

| CN | 1869694 A | 11/2006 |
| CN | 2856983 Y | 1/2007 |

(Continued)

OTHER PUBLICATIONS

Dae-Sik Lee et al., "An Optical Absorbance-based Mult-analytes Detector Using LEDs and an Optical Fiber for a Handheld Digital Urine Reader", 2008 International Symposium and Annual Fall Meeting of the Korean BioChip Society, 2008, pp. 234.

(Continued)

*Primary Examiner* — Peter Macchiarolo
*Assistant Examiner* — Mohammed Keramet-Amircola

(57) ABSTRACT

The present invention relates to a portable digital reader for urinalysis. The portable digital reader for reading an analysis target chip including a plurality of test areas, comprises: a main body including a light emitting section having light emitting elements for radiating light, an integral optical splitter for uniformly distributing the light from the light emitting section to each test area of the analysis target chip, a light receiving section for receiving light reflected from the each test area so as to convert the same to electric signals, and a measuring section for measuring concentration according to the electric signals obtained from the light receiving section; a main supporting body having the analysis target chip and assembled with the main body; and an auxiliary supporting body assembled between the analysis target chip and the main supporting body, including a groove for assembling the analysis target chip, and assembled with the main supporting body to be exchanged after use. Therefore, it is possible to prevent the reader from being contaminated with superfluous urine by forming a portion contacting a strip chip to be exchangeable and disposing a moisture absorption material to a portion for introducing the strip chip.

14 Claims, 5 Drawing Sheets

(51) Int. Cl.
*G01N 21/84* (2006.01)
*G01N 15/06* (2006.01)

(56) References Cited

U.S. PATENT DOCUMENTS

| | | | |
|---|---|---|---|
| 2003/0049175 A1 * | 3/2003 | Buechler et al. | 422/82.08 |
| 2006/0240375 A1 * | 10/2006 | Soukos et al. | 433/29 |
| 2007/0231208 A1 * | 10/2007 | Tanaka et al. | 422/67 |
| 2008/0019867 A1 | 1/2008 | Johnson et al. | |
| 2008/0254405 A1 * | 10/2008 | Montgomery et al. | 433/29 |
| 2009/0191617 A1 * | 7/2009 | Lim et al. | 435/288.7 |

FOREIGN PATENT DOCUMENTS

| | | | | |
|---|---|---|---|---|
| EP | 1 857 804 A2 | 11/2007 | | |
| KR | 1020040095824 A | 11/2004 | | |
| KR | 1020060032778 A | 4/2006 | | |
| KR | 10-2007-0006304 A | 1/2007 | | |
| KR | 1020080052349 A | 6/2008 | | |
| KR | 20-2009-0002043 U | 3/2009 | | |
| KR | 1020100073061 A | 7/2010 | | |
| WO | WO 95/13531 A1 | 5/1995 | | |
| WO | WO 2008/069554 A1 * | 6/2008 | | |
| WO | WO 2008069554 A1 * | 6/2008 | | G01N 21/86 |

OTHER PUBLICATIONS

International Search Report for PCT/KR2010/001386 filed on Mar. 5, 2010.

* cited by examiner

PORTABLE DIGITAL READER FOR URINALYSIS

TECHNICAL FIELD

The present invention relates to a digital reader for urine analysis and, more particularly, to a portable digital reader for urine analysis, which is capable of preventing it from being contaminated by a specimen.

BACKGROUND ART

In general, urine analysis strip chips have a variety of individual test items. Particularly, these test items include occult blood, bilirubin, urobilinogen, ketone body, protein, nitrite, glucose, pH, specific gravity, white blood cell, vitamin C, and so on. Urinalysis using test paper is a semi-quantitative test that primarily screens various body diseases, and can test for abnormalities in their early stages in the body. With this test, it is easy to sample urine, gives no burden to test patients, and allows its results to be immediately determined, so it has become highly utilized. The urine analysis strip chips exhibit test results to the test patient so as to be able to check for abnormalities of the above-mentioned relevant items with the naked eye.

DISCLOSURE

Technical Problem

Since strip chips by nature use testing parts for the respective test items, which are attached to a plastic film, they may have a color region where it is difficult to discriminate a change in color shown as a result of the testing with the naked eye. Thus, the strip chips have a drawback in which test accuracy may be lowered as in the case in which the discrimination in the same color pattern varies depending on an individual such as one who is color blind.

Thus, a reader is used to read information out of these strip chips. The readers, which are on the market at present and are used in hospitals, are bulky and expensive. As such, there is a pressing need to develop diagnostic readers of new concept capable of testing and monitoring health of the public at large anywhere anytime. To this end, readers using light emitting and receiving elements are presented.

However, these readers may leave the user with an unpleasant feeling due to contamination of their bodies caused by residual or excessive urine. Nevertheless, there is no alternative but to manually cope with this problem.

Technical Solution

The present invention is directed to a portable digital reader for urine analysis, in which elements contacting a strip chip can be replaced, thereby making it possible to prevent contamination thereof.

An aspect of the present invention provides a portable digital reader for urine analysis, in which a chip, which is intended for analysis and has a plurality of test regions, is read out. The portable digital reader includes: a body having a light emitter, which includes light emitting elements and emits light, an integrated light distributor uniformly distributing the light from the light emitter to each test region of the chip, a light receiver, which receives the light reflected from each test region and converts the received light into an electric signal, a measuring part, which measures concentration based on the electric signal received from the light receiver, a main support holding the chip and assembled with the body, and an auxiliary support disposed between the chip and the main support, having a recess into which the chip is assembled, assembled with the main support, and replaced after being used.

In exemplary embodiments, the auxiliary support may include a protrusion, which extends from a long side thereof and is placed on the main support.

In exemplary embodiments, the main support may include a recess into which the auxiliary support is assembled.

In exemplary embodiments, the portable digital reader may further include a protective film support, which is mounted on the chip and includes a plurality of windows exposing the test regions.

In exemplary embodiments, the protective film support may include a protrusion aligned with the protrusion of the auxiliary support.

In exemplary embodiments, the protective film support and the auxiliary support may be formed of a polymer.

In exemplary embodiments, the polymer may be one selected from polymethyl methacrylate (PMMA), polyimide (PI), polycarbonate (PC)), and cyclo olefin copolymer (COC), poly ethylene terephthalate (PET), polypropylene (PP) or the like.

In exemplary embodiments, the portable digital reader may further include a loading zone into which the main support is loaded, and a hygroscopic member provided at an upper end of the loading zone and absorbing excessive urine on the chip.

In exemplary embodiments, the hygroscopic member may include a fixing part and a hygroscopic part extending from the fixing part.

In exemplary embodiments, the upper end of the loading zone may include a recess into which the fixing part of the hygroscopic member is assembled.

In exemplary embodiments, the hygroscopic member may be formed of one selected from paper, fiber, polymer, and inorganic material.

In exemplary embodiments, the hygroscopic part may have a U shape or a polygonal shape.

In exemplary embodiments, the portable digital reader may further include a display part for displaying results analyzed by the measuring part.

Advantageous Effects

According to the exemplary embodiment of the present invention, a digital reader can replace elements that are in contact with a strip chip, and dispose a hygroscopic member at a portion into which the strip chip is loaded to prevent it from being contaminated by excessive urine.

DESCRIPTION OF DRAWINGS

The above and other features and advantages of the present invention will become more apparent to those of ordinary skill in the art by describing in detail preferred embodiments thereof with reference to the attached drawings in which.

MODE FOR INVENTION

Figure 1:
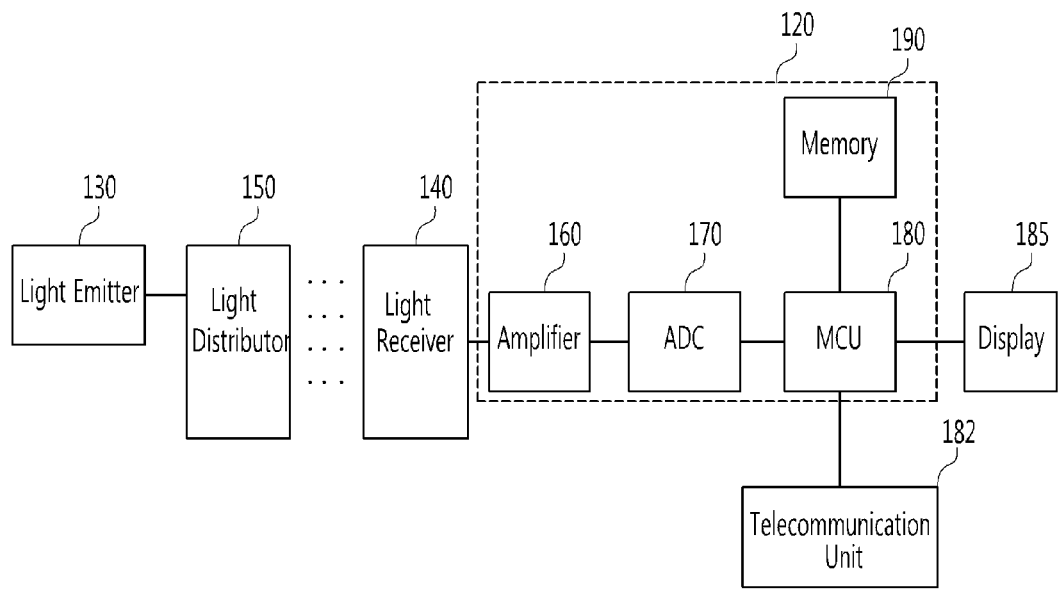
FIG. 1 is a block diagram illustrating a portable digital reader for urine analysis according to an exemplary embodiment of the present invention.

The present invention will be described more fully hereinafter with reference to the accompanying drawings, in which exemplary embodiments of the invention are shown. This invention may, however, be embodied in different forms and should not be construed as limited to the embodiments set forth herein. In order to keep the following description of the present invention clear and concise, detailed descriptions of known functions and components may be omitted. When any element of the invention appears in more than one drawing, it is denoted by the same reference numeral in each drawing.

Figure 2:
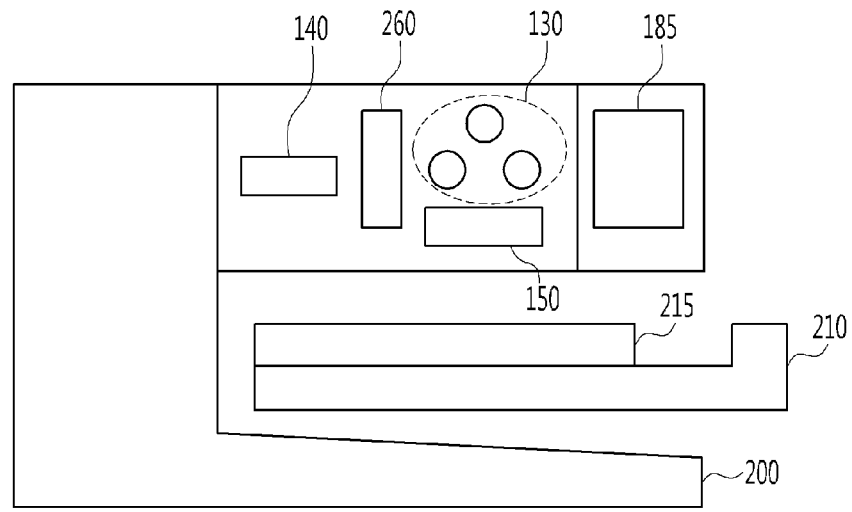
FIG. 2 illustrates a configuration for explaining the structure of a portable digital reader for urine analysis according to an exemplary embodiment of the present invention.

It will be understood that, throughout the specification, unless explicitly stated to the contrary, the term "comprise" and its conjugations such as "comprises" and "comprising" should be interpreted as including any stated elements but not necessarily excluding other elements. In addition, the terms "section," "device," and "module" used herein refer to a unit which can be embodied as hardware, software, or a combination thereof, for processing at least one function and performing an operation. FIG. 1 is a block diagram illustrating a portable digital reader for urine analysis according to an exemplary embodiment of the present invention. FIG. 2 illustrates a configuration for explaining the structure of a portable digital reader for urine analysis according to an exemplary embodiment of the present invention.

Referring to FIG. 1, the portable digital reader for urine analysis includes a light emitter 130 having a three-color light source, a light distributor 150 uniformly transmitting light from the light emitter 130 to each region of a strip chip, a light receiver 140 receiving the light, which is transmitted from the light emitter 130 and is reflected from the strip chip, to perform photoelectric conversion into an electric signal, and a measuring part 120, which measures concentration based on the electric signal received from the light receiver 140.

Further, this digital reader further includes a telecommunication unit 182, and a display 185.

The measuring part 120 includes an amplifier 160, an analog-to-digital converter (ADC) 170, a micro control unit (MCU) 180, a memory 190.

The amplifier 160 amplifies the electric signal received from the light receiver 140, and sends it to the ADC 170. The ADC 170 converts the amplified signal into a digital signal, and sends it to the MCU 180.

The MCU 180 analyzes the digital signal from the ADC 170. Here, the MCU 180 reads chromaticity coordinates of the digital signal to determine the presence of a reaction. Meanwhile, the MCU 180 controls the light emitter 130 in a switching mode.

The memory 190 stores a program driven by the MCU 180, and temporarily stores data calculated by the MCU 180. The display 185 displays the data calculated by the MCU 180, and includes a liquid crystal display, or the like.

The telecommunication unit 182 sends results read out by the MCU 180 to a remote clinic such as a hospital or a public health center, and may include a radio frequency identification system (RFID) chip as a telecommunication module. In this case, the MCU 180 records the results on the RFID chip. When a user intends to send the results to the remote clinic, a user reads the results out of the RFID chip using a wired or wireless terminal on which an RFID reader is mounted, and sends it to a remote terminal.

Further, this reader may include a fluid control module (not shown), which is configured to move, stop, filter, purify, react and mix a micro-fluid in order to make efficient analysis in a bio-chip or strip chip.

The fluid control module includes a channel capable of moving, mixing, and stopping a relevant solution in order to facilitate the analysis of a biological sample, a storage tank storing the fluid, a pump transferring the fluid, a valve controlling the transfer of the fluid, and a mixer for fluid control. In order to move, stop, and mix the fluid, a variety of existing driving means such as an electrostatic motor, a piezoelectric pump, a hydraulic or pneumatic pressure, ultrasonic waves, etc. may be used.

Meanwhile, referring to FIG. 2, the digital reader having the blocks shown in FIG. 1 includes a body 200 and a support 210.

In FIG. 2, the digital reader according to the present invention is to be viewed from the side. The body 200 is formed in a C shape, and the support 210 is taken into or out of a space between opposite lower and upper surfaces of the body 200.

The support 210 has an auxiliary support bio-chip 350 mounted thereon and moves into the body 200.

The body 200 is equipped with a light emitter 130 irradiating each test region of a bio-chip 350 mounted on auxiliary support 215, a light receiver 140, a sidewall 260, a light distributor 150, and a measuring part 120 (not shown) at an upper portion thereof. Further, the body 200 may include a display 185, which displays test results.

The light emitter 130 is configured to combine three-color light emitting diodes (LEDs), i.e. red, blue, and green LEDs.

The three-color light source elements of the light emitter 130 may be discontinuously controlled in a switching mode. For example, the red LED may be operated for a predetermined time, and the signal value R of a photodiode reacting on the light of the red LED may be temporarily stored. Next, the green LED may be operated for a predetermined time, and the signal value G of the photodiode reacting on the light of the green LED may be temporarily stored. Finally, the blue LED may be operated for a predetermined time, and the signal value B of the photodiode reacting on the light of the blue LED may be temporarily stored. By using these stored R, G, and B values, concentration of a target specimen is measured by a value of hue, and it can be checked by a value of intensity whether or not the chip is mounted or the reader is abnormal.

The light receiver 140 may use a silicon sensor such as a silicon photodiode or a phototriode. These sensors may be configured in an array, so that it is possible to secure sensitivity and easy mounting of the bio chip.

The sidewall 260 is provided between the light emitter 130 and the light receiver 140 in order to efficiently discriminate the light, particularly, between the light receiving elements of the light receiver 140.

The light distributor 150 is disposed between the three-color light emitter 130 and the bio chip 350, receives the light from the light emitter 130, and reflects the light such that the light can be uniformly distributed to a plurality of test regions (not shown) in the bio chip 350.

Operation of the digital reader having this configuration will now be described.

When the auxiliary support 215 with a bio chip 350 mounted thereon is inserted into the reader, a switch is turned on, and thus a signal informing that the bio chip 350 is inserted is applied to the MCU 180. When the insertion signal is applied, the MCU 180 determines that the a bio chip 350 is inserted into the reader, thereby applying power to the light emitter 130 made up of three-color LEDs. Here, the MCU 180 applies the power such that the three-color LEDs are discontinuously switched on.

Thereby, the light emitter 130 emits light. The emitted light passes through the light distributor 150, is reflected from each test region of the bio chip 350, and is received by the light receiver 140.

First, whenever the reader is powered on, the signal is compensated for the light source by reading a value of the signal received by the light receiver 140 with respect to initial light source signal intensity of each of the three-color LEDs. For this compensation, a compensator for a white or black color acting as a separate standard color may be further installed in the reader. Thereby, it is possible to obtain precision and reproducibility of the measured signal.

The light receiver 140 converts the received optical signal into an electric signal. The electric signal converted by the light receiver 140 is subject to signal processing and analysis by the MCU 180. The analysis results are displayed through the display 185. Further, the MCU 180 records the readout result on the RFID chip, or enables a user to send the results to a desired remote terminal through a mobile communication modem. Hereinafter, a structure of the support for preventing contamination of the digital reader will be described with reference to FIGS. 3 and 4.

Herein, the support is configured to replace a portion of the strip chip or bio-chip (hereinafter, referred to as "strip chip") which is in contact with the urine in order to prevent contamination of the digital reader.

Figure 3:
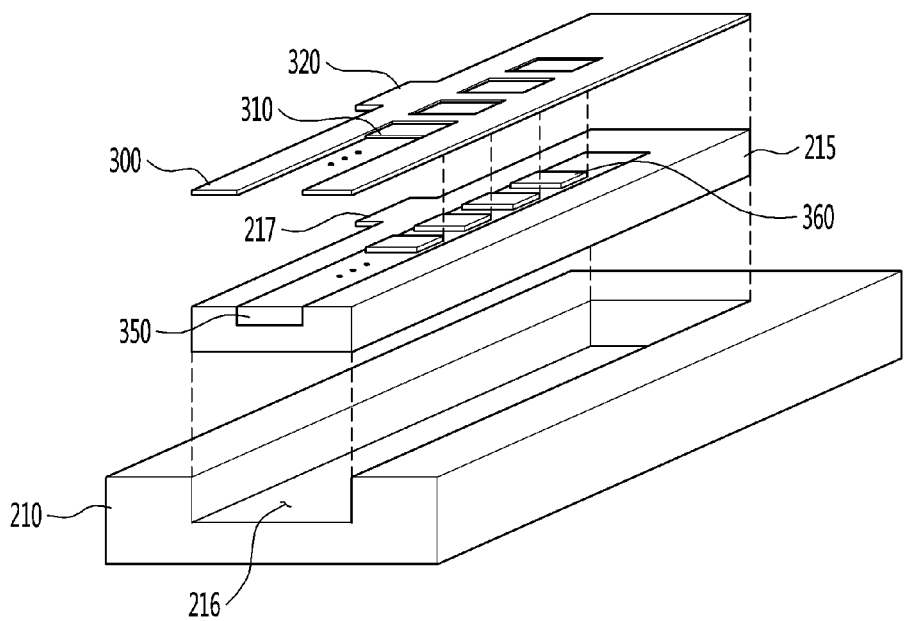
FIG. 3 is a perspective view illustrating the structure of a support on which a strip chip is installed.
Figure 4:
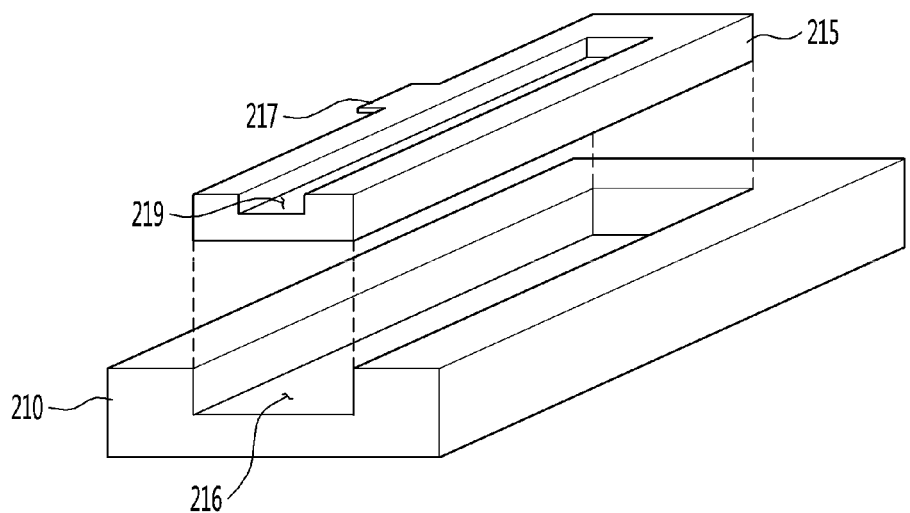
FIG. 4 illustrates the state where the strip chip is removed from the support of FIG. 3.

FIG. 3 is a perspective view illustrating the structure of a support on which a strip chip is installed. FIG. 4 illustrates the state where the strip chip is removed from the support of FIG. 3.

Referring to FIGS. 3 and 4, the support 210 has a long shape in a lengthwise direction of the strip chip 350, and a recess 216 formed therein.

The recess 216 has a long hexahedral shape in the lengthwise direction of the strip chip 350, and an auxiliary support 215 is fitted into the recess 216.

Like the recess 216 of the support 210, the auxiliary support 215 also has a long hexahedral shape in the lengthwise direction of the strip chip 350, and is provided with a recess 219 having the same shape as the strip chip 350.

This auxiliary support 215 includes a protrusion 217 extending outwardly from one side thereof.

In detail, the auxiliary support 215 is closely fitted into the recess 216 of the support 210 when assembled. After the auxiliary support 215 is assembled, the protrusion 217 is placed on the support 210, thereby assisting in separation of the auxiliary support 215. Meanwhile, a protective film support 300 is provided on the auxiliary support 215, and has windows exposing a plurality of test regions 360 of the strip chip 350.

This protective film support 300 has protective film windows 310 and a protrusion 320 like the auxiliary support 215. The protrusion 320 of the protective film support 300 is formed so as to be aligned with the protrusion 217 of the auxiliary support 215.

Meanwhile, the protective film windows 310 of the protective film support 300 may also include a window corresponding to a white or black color compensator for compensating for a white or black color, in addition to the windows for the test regions 360 of the strip chip 350.

In this manner, the protective film support 300 covers a portion other than the test regions 360 of the strip chip 350 so as to prevent urine contamination of the digital reader. The protective film support 300 and the auxiliary support 215 are easily separated from the support 210 by the protrusions 320 and 217 thereof when replaced, so that the user may no longer have an unpleasant feeling of contamination caused by repeated uses.

Here, the windows may be coated to assist in traveling of the light and minimize reflection of the light.

The auxiliary support 215 and the protective film support 300 for preventing contamination may be formed of a polymer. The polymer may include polymethyl methacrylate (PMMA), polyimide (PI)), polycarbonate (PC), cyclo olefin copolymer (COC), poly ethylene terephthalate (PET), polypropylene (PP) or the like.

The auxiliary support 215 and the protective film support 300 may be formed using an existing polymer micromachining technique such as injection molding, hot embossing, casting, or soft lithography, or conventional mechanical techniques, like CNC (computational numerical control) processing.

Meanwhile, the digital reader may also include a module, which absorbs excessive urine in order to prevent contamination. A hygroscopic member will be described with reference to FIGS. 5 through 11.

Figure 5:
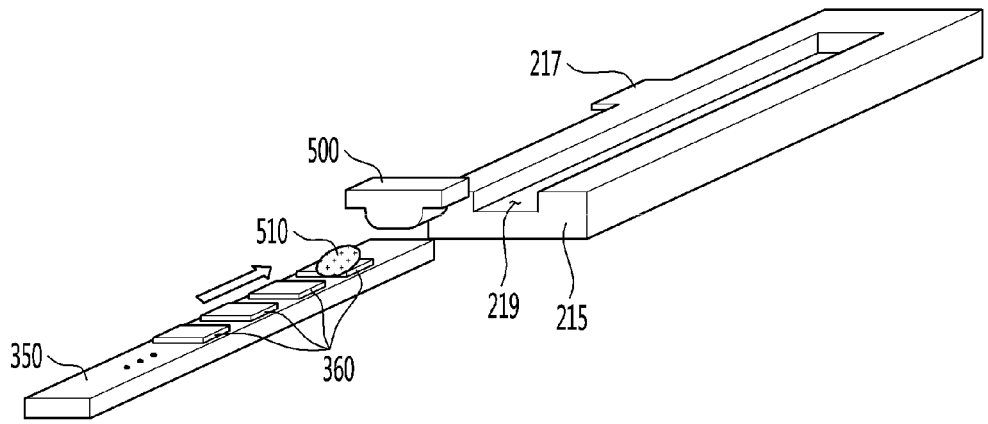
FIG. 5 illustrates the support of a digital reader having a hygroscopic member.
Figure 6:
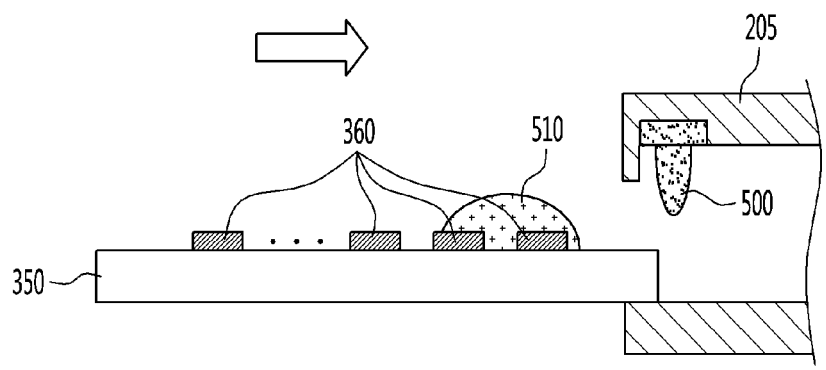
FIG. 6 illustrates a process of loading a support in a digital reader according to a first embodiment of the present invention.
Figure 7:
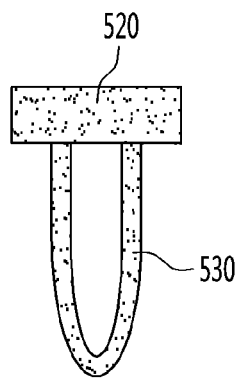
FIGS. 7 through 10 illustrate examples of a hygroscopic member according to the present invention.
Figure 8:
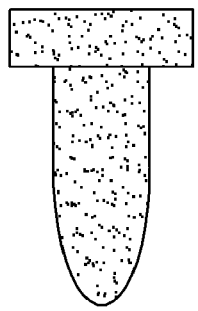
Figure 9:
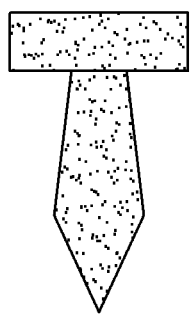
Figure 10:
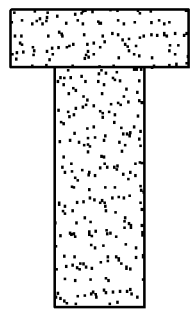
Figure 11:
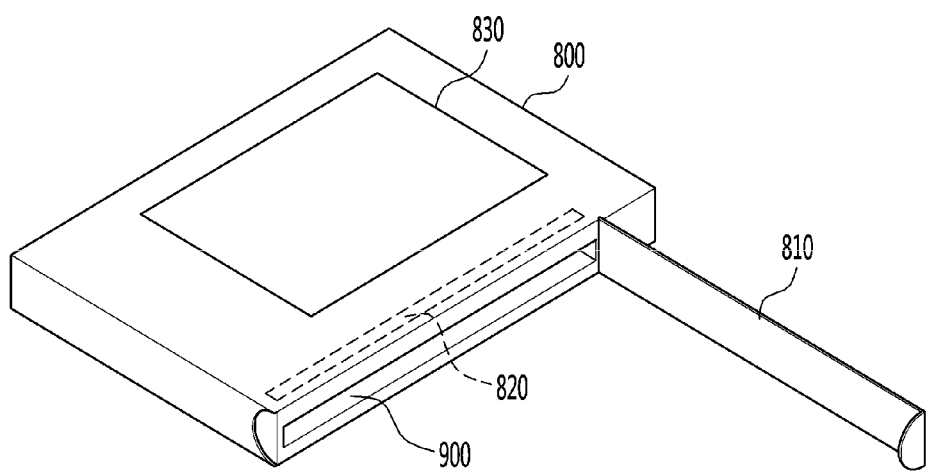
FIG. 11 illustrates a process of loading a support in a digital reader according to a second embodiment of the present invention.

FIG. 5 illustrates the support of a digital reader having a hygroscopic member, and FIG. 6 illustrates a process of loading a support in a digital reader according to a first embodiment of the present invention. FIG. 7 through 10 illustrates examples of a hygroscopic member according to the present invention. FIG. 11 illustrates a process of loading a support in a digital reader according to a second embodiment of the present invention.

Referring to FIGS. 5 and 6, a hygroscopic member 500 is provided at an upper end 205 of the loading zone of a body 200 in order to absorb excessive urine 510 remaining on the strip chip 350.

In detail, as in FIG. 6, when the strip chip 350 assembled on the support (not shown) outside the body 200 is pushed and loaded in a lengthwise direction, the hygroscopic member 500 having a long shape in a downward direction is provided at the upper end 205 of the loading zone of the body 200.

Here, the hygroscopic member 500 is configured of a fixing part 520 and a hygroscopic part 530 as in FIGS. 7 through 10. The hygroscopic part 530 may have a U shape, or a polygonal shape such as a pentagonal shape or a quadrilateral shape. The hygroscopic member 500 may include an organic or inorganic material capable of efficiently absorbing the urine, such as fiber, paper, polymer, or moisture absorbent. As in FIG. 6, the upper end 205 of the loading zone of the body 200 is provided with a recess. The hygroscopic member 500 is assembled for use in such a manner that the fixing part 520 is fixed in the recess and that the hygroscopic part 530 is directed downwards.

In this manner, since the hygroscopic member 500 can be easily assembled or disassembled using the recess formed in the upper end 205 of the loading zone of the body 200, the hygroscopic member 500 removes the excessive urine 510 within the strip chip 350, and then is replaced. Thus, contamination of the digital reader can be prevented.

Meanwhile, as in FIG. 11, the digital reader may have a long loading zone 900 in a lengthwise direction of the strip chip.

The digital reader illustrated in FIG. 11 includes a display window 830 in addition to the long loading zone 900 provided in the lengthwise direction of the strip chip.

In this digital reader, the loading zone 900 is opened by a case 810, and the strip chip is assembled to the support. Here, since the loading zone 900 is in contact with a long side of the strip chip, the hygroscopic member, which is long in the lengthwise direction of the strip chip, is assembled to an upper portion 820 of the loading zone 900. Thereby, contamination caused by excessive urine can be prevented.

In this manner, the hygroscopic member is installed on the upper or lower portion of the loading zone into which the strip chip is loaded, thereby absorbing and removing the excessive urine of the strip chip. Thus, contamination of the digital reader caused by excessive urine can be prevented Here, in the digital reader according to an exemplary embodiment of the present invention, the auxiliary support, the protective film support, and the hygroscopic member, all of which are replaceable, may be all used, or be selectively used.

The exemplary embodiment of the present invention described above can also be implemented as a computer program, or as a recording medium on which a computer program is recorded. This will be easily implemented from the disclosure of the above-mentioned exemplary embodiments of the present invention by those skilled in the art.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A portable digital reader for urine analysis, in which a chip, which is intended for analysis and has a plurality of test regions for urine samples, is read out, the portable digital reader comprising:
a body having a light emitter, which includes light emitting elements and emits light, an integrated light distributor uniformly distributing the light from the light emitter to each test region of the chip, a light receiver, which receives the light reflected from each test region and converts the received light into an electric signal, and a measuring part, which measures concentration based on the electric signal received from the light receiver;
a main support holding the chip and assembled with the body; and
a replaceable auxiliary support disposed between the chip and the main support, the replaceable auxiliary support having a recess into which the chip is assembled, and being assembled with the main support.

2. The portable digital reader according to claim 1, wherein the replaceable auxiliary support includes a protrusion, which extends from a lateral surface of a long side thereof and is placed on the main support.

3. The portable digital reader according to claim 2, wherein the main support includes a recess into which the replaceable auxiliary support is assembled.

4. The portable digital reader according to claim 3, further comprising a removable protective film support, which is mounted on the chip and includes a plurality of windows exposing the test regions.

5. The portable digital reader according to claim 4, wherein the removable protective film support includes a protrusion, which extends from a lateral surface of a long side thereof and is aligned with the protrusion of the replaceable auxiliary support.

6. The portable digital reader according to claim 4, wherein the removable protective film support and the replaceable auxiliary support are formed of a polymer.

7. The portable digital reader according to claim 6, wherein the polymer is one selected from polymethyl methacrylate (PMMA), polyimide (PI), polycarbonate (PC)), cyclo olefin copolymer (COC), poly ethylene terephthalate (PET), and polypropylene (PP).

8. The portable digital reader according to claim 1, further comprising:
a loading zone into which the main support is loaded; and
a hygroscopic member provided at an upper end of the loading zone and absorbing excessive urine on the chip.

9. The portable digital reader according to claim 8, wherein the hygroscopic member includes a fixing part and a hygroscopic part extending from the fixing part.

10. The portable digital reader according to claim 9, wherein an upper end of the loading zone includes a recess into which the fixing part of the hygroscopic member is assembled.

11. The portable digital reader according to claim 10, wherein the hygroscopic member is formed of one selected from paper, fiber, polymer, and inorganic material.

12. The portable digital reader according to claim 11, wherein the hygroscopic part has a U shape or a polygonal shape.

13. The portable digital reader according to claim 1, further comprising a display part for displaying results analyzed by the measuring part.

14. The portable digital reader according to claim 1, further comprising:
a loading zone extending in a long direction of the portable digital reader, the loading zone including an upper surface of the portable digital reader, and being provided at a front portion of the portable digital reader; and
a hygroscopic member coupled to the upper surface of the portable digital reader in the loading zone.

* * * * *